United States Patent
Boodaghians

(10) Patent No.: US 9,296,480 B2
(45) Date of Patent: Mar. 29, 2016

(54) USE OF AT LEAST ONE OUTPUT OF A FUEL CELL SYSTEM IN A LAVATORY

(71) Applicant: MAG Aerospace Industries, LLC, Carson, CA (US)

(72) Inventor: Razmik Boodaghians, Glendale, CA (US)

(73) Assignee: MAG Aerospace Industries, LLC, Carson, CA (US)

( * ) Notice: Subject to any disclaimer, the term of this patent is extended or adjusted under 35 U.S.C. 154(b) by 0 days.

(21) Appl. No.: 14/375,813

(22) PCT Filed: Mar. 13, 2013

(86) PCT No.: PCT/US2013/030638
§ 371 (c)(1),
(2) Date: Jul. 31, 2014

(87) PCT Pub. No.: WO2013/142161
PCT Pub. Date: Sep. 26, 2013

(65) Prior Publication Data
US 2015/0013063 A1    Jan. 15, 2015

Related U.S. Application Data

(60) Provisional application No. 61/612,504, filed on Mar. 19, 2012.

(51) Int. Cl.
*B64D 11/02* (2006.01)
*B64D 41/00* (2006.01)
(Continued)

(52) U.S. Cl.
CPC . *B64D 11/02* (2013.01); *A61L 2/20* (2013.01); *B61D 35/007* (2013.01); *B64D 41/00* (2013.01);
(Continued)

(58) Field of Classification Search
CPC ......... B64D 11/02; B64D 41/00; H01M 8/00; A61L 2/20
USPC ...................................................... 4/663, 664
See application file for complete search history.

(56) References Cited

U.S. PATENT DOCUMENTS 8,141,185 B2    3/2012  Hoffjann et al.
8,615,418 B1 *  12/2013  Niznik ................... G06Q 10/02
                                                701/120
(Continued)

FOREIGN PATENT DOCUMENTS

CA    2406118    * 10/2001    ........... A62C 3/0221
CA    2700658 A1    4/2009
(Continued)

OTHER PUBLICATIONS

PCT/US2013/030638, Search Report and Written Opinion dated Jun. 20, 2013, 10 pages.
(Continued)

*Primary Examiner* — J. Casimer Jacyna
(74) *Attorney, Agent, or Firm* — Kilpatrick Townsend & Stockton LLP; Dean W. Russell, Esq.; Renae Bailey Wainwright, Esq.

(57) ABSTRACT

In a craft such as an aircraft, a lavatory unit may be powered by the various outputs of a fuel cell system, including by-products that typically become waste. For example, but not limited to, a combination of the water, oxygen-depleted air, thermal energy and/or electrical energy generated by the fuel cell system may be used to supply water to the faucet and the toilet of the lavatory unit, to supply the lavatory unit with its electrical needs, and to heat and/or disinfect and/or dry the lavatory unit and its surfaces.

17 Claims, 4 Drawing Sheets

(51) Int. Cl.
  *B61D 35/00* (2006.01)
  *A61L 2/20* (2006.01)
  *H01M 8/00* (2006.01)

(52) U.S. Cl.
  CPC ........... *H01M 8/00* (2013.01); *B64D 2041/005* (2013.01); *Y02T 30/30* (2013.01); *Y02T 50/44* (2013.01); *Y02T 50/46* (2013.01); *Y02T 90/36* (2013.01)

(56) References Cited

U.S. PATENT DOCUMENTS

| | | |
|---|---|---|
| 2004/0043276 A1 | 3/2004 | Hoffjann et al. |
| 2004/0057177 A1 | 3/2004 | Glahn et al. |
| 2006/0138278 A1 | 6/2006 | Gans |
| 2007/0119699 A1* | 5/2007 | Chambers .............. A61L 9/015 204/176 |
| 2007/0172707 A1 | 7/2007 | Hoffjann et al. |
| 2008/0001026 A1 | 1/2008 | Hoffjann et al. |
| 2008/0038597 A1 | 2/2008 | Hoffjann et al. |
| 2008/0133076 A1 | 6/2008 | Formanski et al. |
| 2010/0193629 A1* | 8/2010 | Breit ..................... B64D 11/02 244/58 |
| 2010/0221642 A1 | 9/2010 | Frahm et al. |
| 2013/0200216 A1* | 8/2013 | Mock .................. H01M 8/0662 244/135 R |
| 2013/0210329 A1 | 8/2013 | God et al. |

FOREIGN PATENT DOCUMENTS

| | | |
|---|---|---|
| DE | 102006042300 B4 | 9/2008 |
| DE | 102007054291 A1 | 4/2009 |
| EP | 2213571 A2 | 8/2010 |
| WO | 2006058774 A2 | 6/2006 |
| WO | 2007039211 A1 | 4/2007 |
| WO | 2007057188 A1 | 5/2007 |
| WO | 2011089016 A2 | 7/2011 |

OTHER PUBLICATIONS

International Patent Application No. PCT/US2013/030638, International Preliminary Report on Patentability dated Oct. 2, 2014, 7 pages.

Chinese Patent Application 201380009985.5, Office Action (and English translation) dated Jul. 24, 2015.

* cited by examiner

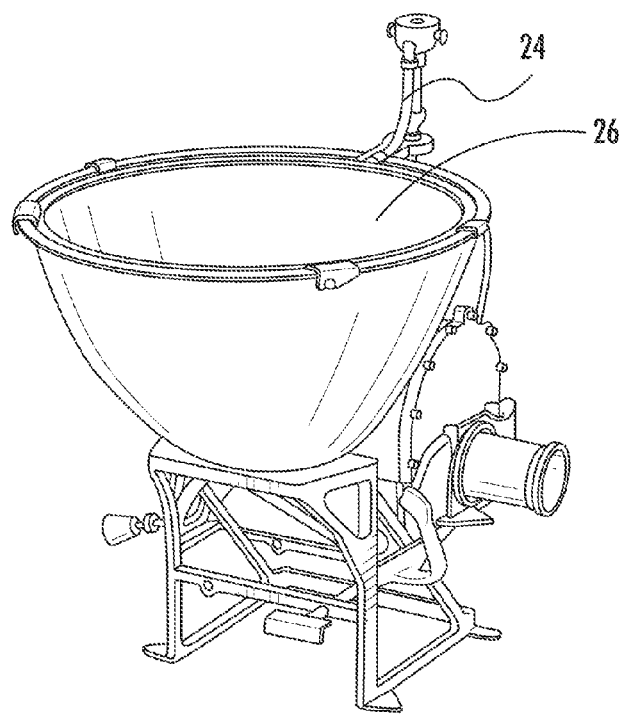
FIG. 5
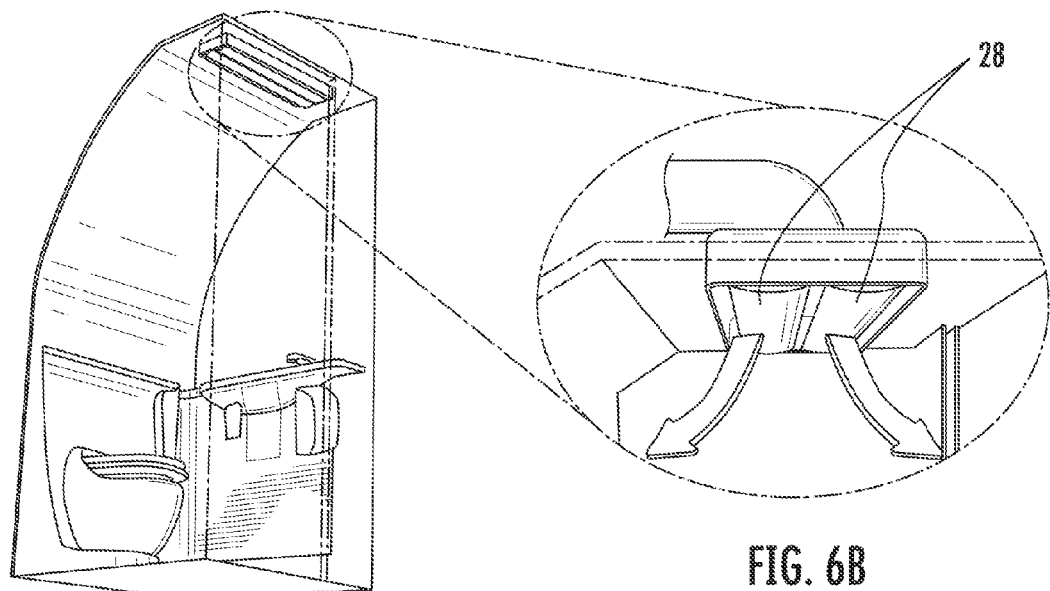
FIG. 6A
FIG. 6B

USE OF AT LEAST ONE OUTPUT OF A FUEL CELL SYSTEM IN A LAVATORY

CROSS REFERENCE TO RELATED APPLICATIONS

This application is the U.S. national phase of International Application No. PCT/US2013/030638 filed on Mar. 13, 2013 and titled "Fuel Cell System Powered Lavatory," which claims priority benefits from U.S. Provisional Application Ser. No. 61/612,504 filed on Mar. 19, 2012 and titled "Fuel Cell Powered Lavatory," the entire contents of both of which are incorporated herein by reference.

FIELD OF THE INVENTION

Systems and methods relate to lavatories powered by fuel cell systems.

BACKGROUND

A number of components on-board an aircraft require electrical power for their activation. Many of these components are separate from the electrical components that are actually required to run the aircraft (i.e., the navigation system, fuel gauges, flight controls, and hydraulic systems). For example, aircraft also have catering equipment, heating/cooling systems, lavatories, power seats, water heaters, and other components that require power as well. Specific components that may require external power include, but are not limited to, trash compactors (in galley and/or lavatory), surface cleaning, area heaters, cabin ventilation, independent ventilation, area or spot lights (e.g., cabin lights and/or reading lights for passenger seats), water supply, water line heating to prevent freezing, charging stations for passenger electronics, electrical sockets, vacuum generators, vacuum toilet assemblies, grey water interface valves, emergency lighting, and combinations thereof.

Currently, lavatory units on aircrafts are powered by the ground power unit or the aircraft power generation system (such as the aircraft's engines or auxiliary power units (APU)). In some cases, the power generation unit requires fossil fuels, is noisy, and emits $CO_2$. Also in some cases, such systems require more power than can be drawn from the aircraft engines' drive generators, necessitating additional power sources, such as a kerosene-burning auxiliary power unit (APU) (or by a ground power unit if the aircraft is not yet in flight). If additional power sources are used, passengers are unable to use the lavatory until the APU or ground power unit is turned on. The power consumption of the lavatory can be rather large, particularly for long flights with hundreds of passengers. Moreover, in some cases, the power must travel a long distance to reach the point of use, which can lead to power dissipation.

Moreover, operation of the lavatory requires water, so the lavatory must be connected by pipes or otherwise to the aircraft's main potable water tank. For example, coffee cannot be made, passengers cannot use the lavatories, hand-washing water is not provided, and so forth, until the APU or electrical switch is on in order to allow water to flow. Some examples of the water consumers on-board aircraft in the lavatory unit are the tap water supply and the toilet vacuum system. Aircraft typically carry large amounts of potable water in the potable water tanks, which is uploaded when the aircraft is on the ground. The lavatory unit also sometimes requires heat, which is also typically generated by separate units. For example, heated water is desirable for use in warming hand-washing water (and to prevent freezing of the water pipes), as well as the cabin heating units.

The relatively new technology of fuel cell systems combines a fuel source of compressed hydrogen with oxygen in the air to produce electrical energy as a main product. As shown in FIG. 4, a fuel cell system has several outputs in addition to electrical power, and these other outputs often are not utilized and therefore become waste. For example, thermal power (heat), water and oxygen-depleted air (ODA) are produced as by-products. These by-products are far less harmful than $CO_2$ emissions from current aircraft power generation processes.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

Disclosed is a lavatory unit powered by at least one of a fuel cell system's outputs, such as electrical energy, thermal energy, water, and/or oxygen-depleted air. In some embodiments, the lavatory unit is powered by two or three or more of the outputs of the fuel cell system. According to some embodiments, the fuel cell system is positioned proximate the lavatory unit and water of the fuel cell system is directed by a plurality of conduits to appropriate areas or occupants of the lavatory unit.

Also disclosed is a method of using a fuel cell system to power a lavatory unit associated with an aircraft by directing water and/or electrical energy and/or thermal energy and/or oxygen-depleted air generated by the fuel cell system to appropriate areas or occupants of the lavatory unit.

Also disclosed is a method of using outputs of a fuel cell system (such as water, electrical energy, thermal energy, and/or oxygen-depleted air) to clean an aircraft lavatory unit.

BRIEF DESCRIPTION OF THE DRAWINGS

The specification makes reference to the following appended figures, in which use of like reference numerals in different figures is intended to illustrate like or analogous components.

FIG. 5 is a perspective view of a storage tank in communication with a fuel cell system, according to one embodiment.

FIGS. 6A-B illustrate a portion of a lavatory unit according to one embodiment as at least one by-product of a fuel cell system is directed into the lavatory unit.

DETAILED DESCRIPTION

Disclosed herein are systems and processes for providing lavatories that are powered by fuel cell systems or other suitable power sources. While the lavatories are discussed for use in aircrafts, they are by no means so limited and may be used in buses, trains, or other forms of transportation equipped with a lavatory. The lavatories discussed herein also may be stand-alone restrooms or portable restrooms used in any other suitable environment. When powered by an appropriate fuel cell system, the lavatory's operation can be made independent of (or less dependent on) the vehicle's (or surrounding environment's) electrical power system.

Figure 1:
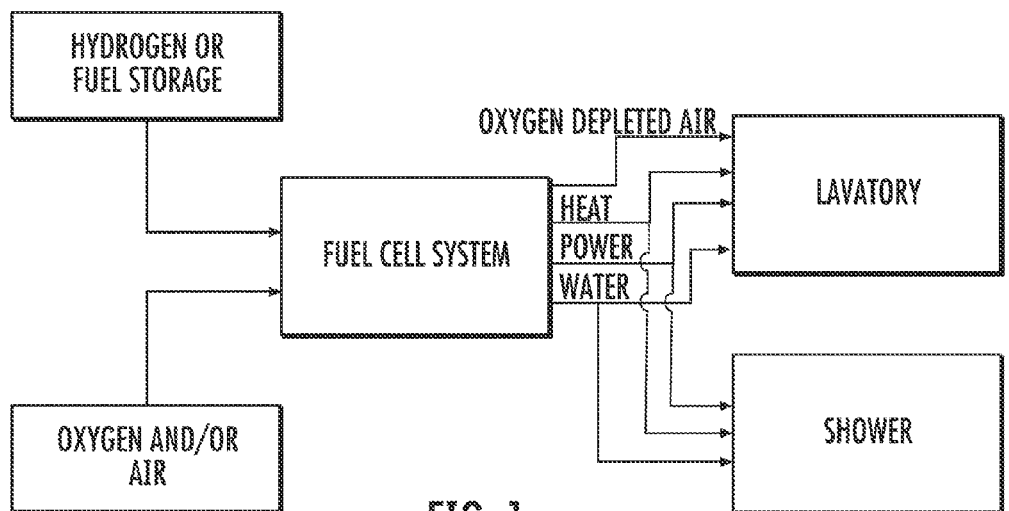
FIG. 1 is a diagram illustrating the inputs and outputs of a fuel cell system and non-limiting examples of how the outputs might be used.
Figure 4:
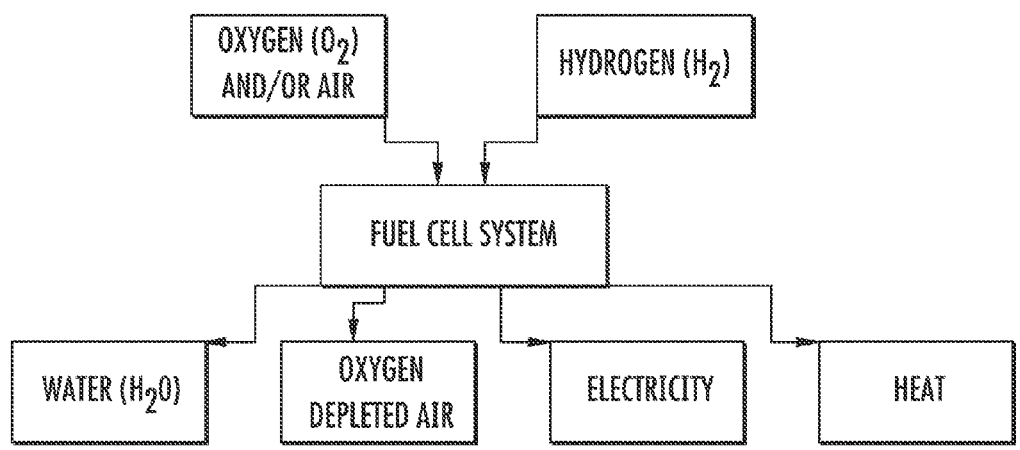
FIG. 4 shows a schematic example of input elements that may be used for a fuel cell and the output elements ($H_2O$, electricity, oxygen depleted air (ODA), and heat).

A fuel cell system is a device that converts chemical energy from a chemical reaction involving hydrogen or other fuel source and oxygen rich gas (e.g., air) into electrical energy. As illustrated in FIG. 1, hydrogen or another fuel source combines with oxygen in a fuel cell system to generate electrical energy (power). As shown in FIG. 4, along with the generated electrical energy, the fuel cell system produces water, thermal power (heat), and oxygen-depleted air (ODA) as by-products. As disclosed herein, some or all of the electrical energy, heat, water, and ODA may be used to power a lavatory, such as but not limited to, a lavatory used in an aircraft.

Any appropriate fuel cell system may be used, including, but not limited to, a Proton Exchange Membrane Fuel Cell (PEMFC), a Solid Oxide Fuel Cell (SOFC), a Molten Carbonate Fuel Cell (MCFC), a Direct Methanol Fuel Cell (DMFC), an Alkaline Fuel Cell (AFC), or a Phosphoric Acid Fuel Cell (PAFC). Any other existing or future fuel cell system technology, including but not limited to a hybrid solution, may also be used.

Figure 2:
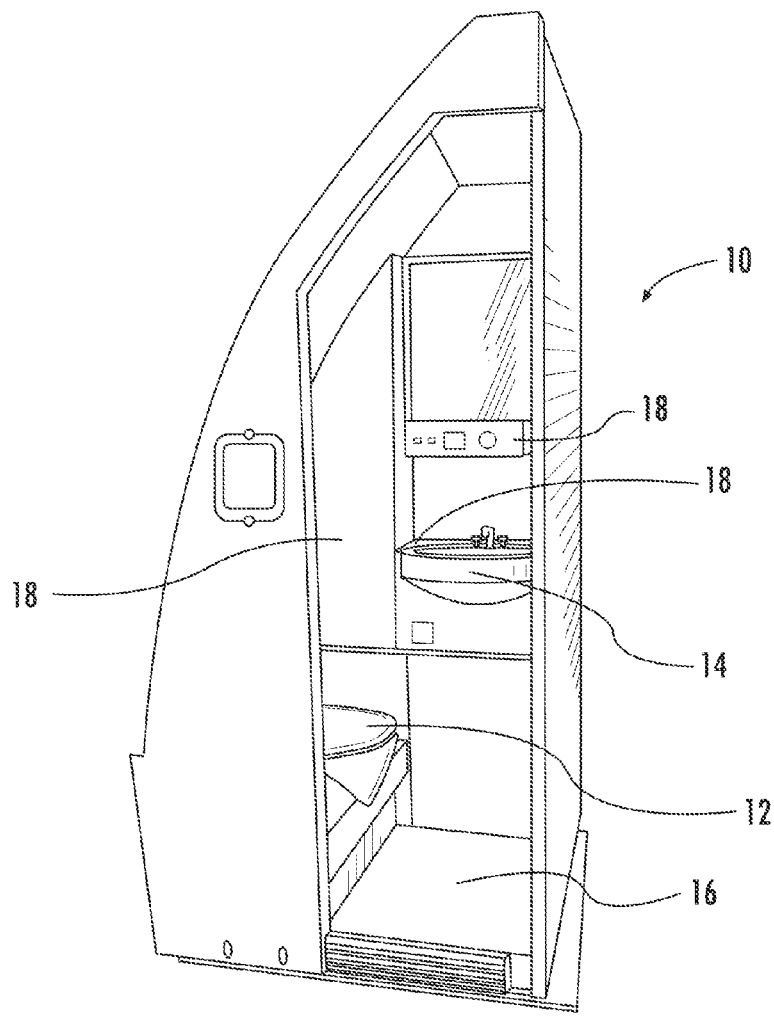
FIG. 2 is a perspective front view of a lavatory unit configured to be powered by a fuel cell system according to one embodiment.
Figure 3:
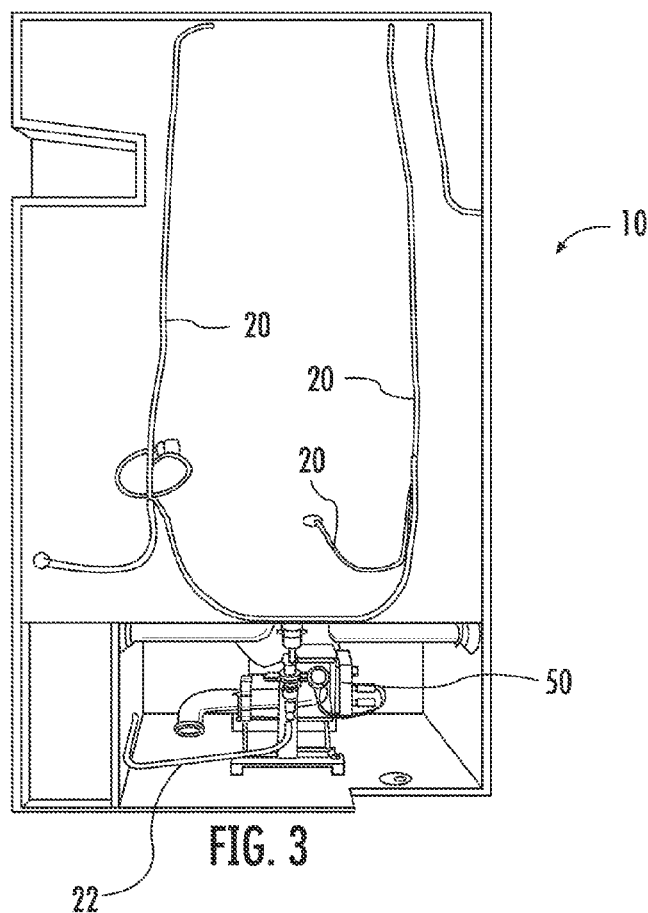
FIG. 3 is a perspective rear view of the lavatory unit of FIG. 2.

FIGS. 2-3 illustrate a non-limiting embodiment of a lavatory unit 10 configured to be powered by a fuel cell system, such as fuel cell system 50 shown in FIG. 3, or any other suitable fuel cell system. As shown in FIG. 2, lavatory unit 10 may include a toilet 12, a wash basin 14, a floor 16, and various surfaces 18. In other embodiments, lavatory unit 10 may include a shower, a hair dryer, a hand dryer, a baby changing station, a trash compactor, and any other suitable feature or element, some of which are discussed below.

As illustrated in FIG. 3, various conduits 20 (which may be pipes, hoses, or other suitable lines) may connect the fuel cell system (such as fuel cell system 50) with the lavatory unit 10. In some embodiments, an input conduit 22 may be used to direct water from the fuel cell system into a tank (for example, but not limited to, tank 26 shown in FIG. 5) for storage and an output conduit 24 (FIG. 5) may be used to direct the stored water from the storage tank to the appropriate conduit or area of the lavatory unit. In other embodiments, a tank is not used and water is directed from the fuel cell system to the lavatory unit directly. Water may be directed to the faucet of the wash basin 14 for hand or other washing, to the toilet 12, or to a shower (not pictured), or may be directed for other purposes. Depending on the location of the fuel cell system, a pump or other suitable mechanism may be used to distribute the water to the appropriate area of the lavatory unit. If the fuel cell system is positioned above the appropriate area, the water may be permitted to flow by gravity to the appropriate area.

In some embodiments, water directed to the wash basin that has been used may be recovered, treated with ultraviolet light or otherwise, and directed to the toilet. In some cases, water from the fuel cell system (or used water from the wash basin) is directed to the waste holding tank to flush any waste stored within.

Although the fuel cell system and the storage tank may be part of the lavatory unit 10, the fuel cell system and/or storage tank may be located in any suitable location on the aircraft. For example, a fuel cell system used to power other aspects of an aircraft may also be used to power the lavatory, or a separate fuel cell system may be used to power the lavatory. Power needed by the lavatory may be supplied directly by one or more fuel cell systems or may be supplied or supplemented by any suitable electrical energy storage (such as batteries or supercapacitors, etc.) charged by power generated from a fuel cell system or otherwise. Supplemental power may also be supplied by a typical power source in an aircraft such as the ground power unit or the aircraft power unit.

If the fuel cell system is positioned within or near the lavatory unit, the power is generated near the point of use and does not need to travel a long distance and therefore power dissipation is minimized. Moreover, if the fuel cell system is positioned within or near the lavatory, the fuel cell system may also be used to power other aircraft systems such as, but not limited to, passenger seats, passenger entertainment systems, emergency lighting, reading lights, the galley, etc., whether or not these systems are in the vicinity of the lavatory, so that the required energy/power output is more stable and there is less energy waste.

More than one fuel cell system may be used if needed, and the size of the one or more fuel cell systems may be based on the energy/power requirements of the lavatory and/or other systems. In some embodiments, the fuel cell system optionally may include, among other things, ancillaries such as a battery system, a capacitor bank, and/or a power management system to help reduce the required energy/power output of the fuel cell system by helping to efficiently absorb peak energy/power demands.

In embodiments where one or more separate fuel cell systems are used to power the lavatory, as shown in FIGS. 2-3, the water storage tank (such as but not limited to tank 25 shown in FIG. 5) optionally may be in communication with the aircraft's main potable water tank. In this way, if the water generated from the fuel cell system is not sufficient to meet water needs in the lavatory unit, water from the aircraft's main water tank can be utilized as well. Also, surplus water generated from the fuel cell system may be directed into the aircraft's main potable water tank. Hot water from the fuel cell system may also be introduced into the main potable water tank to dilute (cool) the fuel cell system hot water to a suitable temperature and/or to heat the water already stored in the main potable water, depending on the volume involved.

A fuel cell system, such as fuel cell system 50, produces moisture as a by-product. A heat exchanger may be used to condense the moisture and recover water from it. The heat exchanger may also be used to cool the water so it is suitable for use for showering, hand or face or other body washing, waste holding tank flushing, and the like. Since the water recovered from the fuel cell system is between approximately 65 degrees Celsius and approximately 80 degrees Celsius, using water from the fuel cell system in the lavatory wash basins and/or showers eliminates the need for water heaters that are typically used to heat water supplied to a lavatory, which reduces costs and storage space requirements and conserves energy. If used, the heat exchanger may include controls so that the hot water recovered from the fuel cell system may be cooled to the appropriate and/or desired temperature.

Once the water has been recovered from the moisture, it optionally may be directed into a storage tank as discussed above and/or may be further treated. For example, the water may be subjected to ultraviolet light to destroy any pathogens in the water. Alternatively or additionally, the water may be treated with chlorine, filtered, or otherwise processed to remove bacteria or other pathogens.

Another by-product of the fuel cell system is hot oxygen-depleted air. The hot ODA is produced at a temperature sufficient to dry and/or sanitize and/or heat surfaces 18 of the lavatory, such as the toilet seat, the sink area, the floor, any handles, the trash bin, and any other desired surface such as but not limited to surfaces of a baby changing station.

In some cases, the ODA as produced by the fuel cell system contains moisture, and a condenser or other suitable mechanism may be used to remove the moisture or otherwise dry the ODA before use. As shown in FIGS. 6A-B, the hot ODA (and/or heat) from the fuel cell system may be directed through air ducts 28 in the ceiling or other suitable location into the lavatory unit. The hot ODA and/or heat may be used to heat the lavatory unit and/or its surfaces, to dry any wet surfaces, and/or kill any pathogens in the air or on any surfaces. In some embodiments, the hot ODA and/or heat is directed through the ducts and into the lavatory unit periodically, such as in regular or irregular bursts. In some embodiments, the lavatory unit 10 is locked so that passengers are unable to enter the lavatory unit during this cleaning process.

Figure 7:
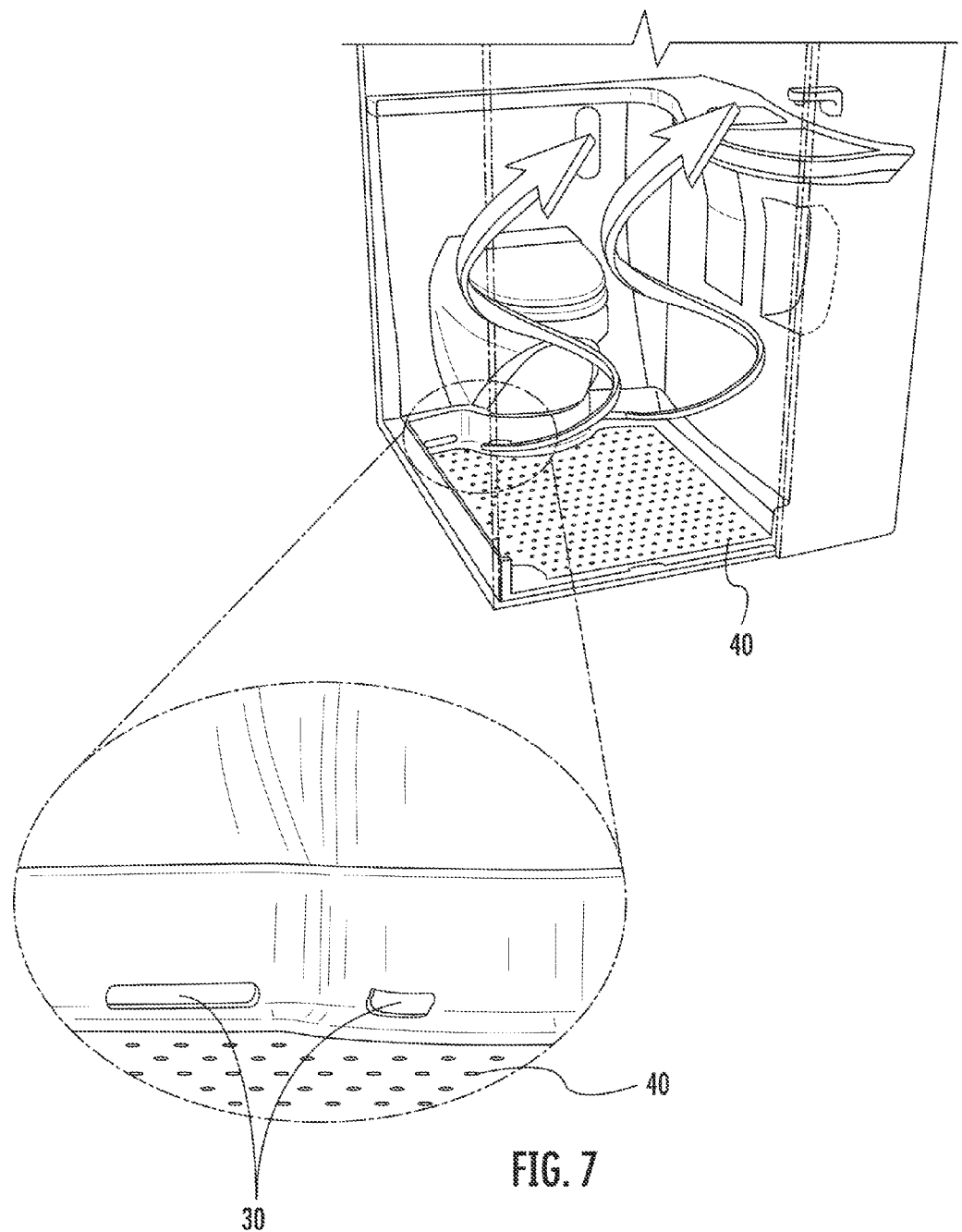
FIG. 7 illustrates a portion of a lavatory unit according to another embodiment as at least one by-product of a fuel cell system is directed into the lavatory unit.

As shown in FIG. 7, ODA (and/or heat) from the fuel cell system may be directed into the lavatory unit through shrouds or other outlets 30 proximate the floor and/or outlets in or along the floor, such as but not limited to micro holes 40 along the floor of the unit, which may be used to heat, dry and/or sanitize the floor before migrating upwards to dry, heat, and/or sanitize other surfaces within the unit.

In some embodiments, the hot ODA and/or heat may be used instead of, or in addition to, electrical hand or hair dryers to dry a person's hands or hair. The hot ODA and/or heat could also be directed to warm and/or sanitize and/or dry the surfaces of a baby changing station. The hot ODA and/or heat may also be used to heat the lavatory unit itself.

The hot ODA could be treated before or upon entering the lavatory unit. For example, oxidizers, fragrances, and/or air ionizers or the like could be mixed with the ODA to help eliminate odors and pathogens. In essence, the hot ODA being pushed into the lavatory unit could help replace stale, odor-filled air with new air. In this way, the ODA may provide independent ventilation for the lavatory unit. In some embodiments, the ODA could be used as a vacuum generator.

As mentioned, the fuel cell system also generates electrical energy that may be used in the lavatory unit. Some non-limiting uses of the electrical energy generated from the fuel cell system include: (1) lighting the lavatory (via area or spot lights); (2) operating a smoke detector or fire extinguishing system; (3) operating an electrical hand or hair dryer; (4) lighting a sign indicating a status of the lavatory (e.g., but not limited to, that the lavatory is being cleaned and/or is occupied and/or is unoccupied and/or has been cleaned and/or is out of service); (5) providing power for an electrical socket; (6) operating a water pump, heat exchanger and/or lavatory trash compactor; or (7) automatically locking and unlocking the door to the lavatory unit. The power generated from the fuel cell system can be used in any other suitable way in which traditional electricity is used in a lavatory. For example, the electric energy could also be used to heat the toilet seat, heat cold water (for example, from the aircraft's main water tank) for use in the wash basin or shower, or for any other suitable purpose. In some cases, the electrical energy generated from the fuel cell system is used to meet some or all of the electric power requirements of the lavatory.

Each of the fuel cell system by-products described above may be used alone or in combination with other by-products or other power sources to meet various needs of the lavatory unit. As one of many examples, the water and/or ODA and/or heat by-products may be used for surface cleaning. One or both of the power and water generated may be used as a grey water interface valve and for water line heating. Moreover, the lavatory trash compactor described above may use both heat and electrical energy generated from the fuel cell system.

The lavatory unit may be used in the main cabin of the aircraft, in a first class cabin, or may be configured to fit in a crew resting compartment to improve the facilities offered to the crew during their rest period. The lavatory unit may be used on commercial or private aircraft.

Using a fuel cell system to power a lavatory as described above may reduce the use of fossil fuels and also reduce noise and $CO_2$ emissions. In some embodiments, some or all of the by-products of the fuel cell system are utilized to power a lavatory unit, thus increasing the efficiency of the fuel cell system. In addition, using water recovered from the fuel cell system in the lavatory and otherwise can reduce the amount of water that needs to be brought onto the aircraft and stored in potable water tanks, which in turn can reduce the weight of the aircraft and lead to cost savings during takeoff and during flight. Moreover, reducing the amount of water required to be stored the potable water tanks means a smaller water tank may be used, which results in both a lighter water tank and less space being allocated to house the water tank.

The foregoing is provided for purposes of illustrating, explaining, and describing embodiments of the invention. Further modifications and adaptations to these embodiments will be apparent to those skilled in the art and may be made without departing from the scope or spirit of the invention. As one example, instead of a fuel cell system, another suitable power source that is independent from the aircraft's main power system may be used.

The invention claimed is:

1. A lavatory unit that uses at least one output of a fuel cell system,
   wherein the at least one output comprises a combination of thermal energy and oxygen-depleted air that is directed from the fuel cell system into the lavatory unit to heat, dry, and sanitize surfaces of the lavatory unit, and
   wherein the at least one output further comprises electrical energy that locks a door to the lavatory unit while the combination of thermal energy and oxygen-depleted air is being directed into the lavatory unit.

2. The lavatory unit of claim 1, wherein the lavatory unit is further supplied by water generated by the fuel cell system.

3. The lavatory unit of claim 1, wherein the fuel cell system is proximate the lavatory unit and water supplied by the fuel cell system is directed by at least one conduit to appropriate areas within the lavatory unit.

4. The lavatory unit of claim 1, wherein the oxygen-depleted air is directed into the lavatory unit via shrouds or ducts in a floor or a ceiling of the lavatory unit.

5. The lavatory unit of claim 3, wherein the water supplied by the fuel cell system is directed to a toilet or a faucet.

6. The lavatory unit of claim 1, wherein the lavatory unit is configured for use in an aircraft.

7. The lavatory unit of claim 3, further comprising a water treatment unit that disinfects the water before it is directed to the appropriate areas.

8. A method of using a fuel cell system to clean and power a lavatory unit for use in an aircraft comprising:
   (1) locking a door to the lavatory unit using electrical energy generated by the fuel cell system;
   (2) directing both thermal energy and oxygen-depleted air generated by the fuel cell system to the lavatory unit to sanitize, heat, deodorize and/or dry the lavatory unit or surfaces of the lavatory unit; and
   (3) unlocking the door to the lavatory unit.

9. The method of claim 8, further comprising directing water supplied by the fuel cell system to at least one of a toilet, a basin, or a shower.

10. The method of claim 9, wherein gravity directs the water to the lavatory unit.

11. The method of claim 9, wherein a mechanism directs the water to the lavatory unit.

12. The method of claim 9, further comprising treating the water supplied by the fuel cell system before or after directing it to the lavatory unit.

13. The method of claim 8, further comprising treating the oxygen-depleted air before directing it to the lavatory unit.

14. A method of using outputs of a fuel cell system to clean an aircraft lavatory unit comprising:
   using electrical energy generated by the fuel cell system to lock a door to the lavatory unit and to light a status display indicating at least that the lavatory unit is unavailable for use or is being cleaned;
   using at least one of water, thermal energy, or oxygen-depleted air generated by the fuel cell system to sanitize surfaces of the lavatory unit;
   using at least one of the thermal energy or the oxygen-depleted air to dry the surfaces of the lavatory unit; and
   deactivating the status display and unlocking the door to the lavatory unit.

15. The method of claim 14, further comprising activating the status display to indicate that the lavatory unit has been cleaned.

16. The lavatory unit of claim 1, wherein the electrical energy further lights a status display to indicate at least one of following statuses: (1) that the lavatory unit is being cleaned and (2) that the lavatory unit has been cleaned.

17. The lavatory unit of claim 1, further comprising a status display that is configured to be lit by the electrical energy to indicate at least one of following statuses: (1) that the lavatory unit is being cleaned and (2) that the lavatory unit has been cleaned.

* * * * *